United States Patent
Liu et al.

(10) Patent No.: US 8,835,674 B2
(45) Date of Patent: Sep. 16, 2014

(54) CONJUGATED DIENE PHOSPHINATE COMPOUNDS, PREPARATION METHOD AND USE THEREOF

(75) Inventors: Zhaoqing Liu, Shanghai (CN); Floryan De Campo, Shanghai (CN)

(73) Assignee: Solvay (China) Co., Ltd., Shanghai (CN)

( * ) Notice: Subject to any disclaimer, the term of this patent is extended or adjusted under 35 U.S.C. 154(b) by 3 days.

(21) Appl. No.: 13/502,901

(22) PCT Filed: Oct. 30, 2009

(86) PCT No.: PCT/CN2009/074730
§ 371 (c)(1),
(2), (4) Date: Apr. 19, 2012

(87) PCT Pub. No.: WO2011/050537
PCT Pub. Date: May 5, 2011

(65) Prior Publication Data
US 2012/0208975 A1    Aug. 16, 2012

(51) Int. Cl.
*C07F 9/30*    (2006.01)

(52) U.S. Cl.
USPC .................................................. 562/8

(58) Field of Classification Search
USPC .................................................. 562/8
See application file for complete search history.

(56) References Cited

U.S. PATENT DOCUMENTS

| | | | |
|---|---|---|---|
| 4,605,779 A | 8/1986 | Matsuda et al. | |
| 6,156,859 A | 12/2000 | Langstein | |
| 6,329,544 B1 | 12/2001 | Weferling et al. | |
| 6,902,608 B2 | 6/2005 | Erdmann et al. | |

FOREIGN PATENT DOCUMENTS

| | | | |
|---|---|---|---|
| JP | 2005232067 | * | 9/2005 |
| SU | 242383 | * | 9/1969 |

OTHER PUBLICATIONS

Prashad, M. "Phosphonate vs. phosphinate elimination during olefination of aldehydes" Tetrahedron Letters, vol. 34, p. 1585-1588, 1993.*
Machine translation of JP 2005232067, p. 1-8, Sep. 2005.*
English translation of SU 242383, 1969, p. 1-7.*
Prashad, Mahavir "Phosphonate vs. phosphinate elimination during olefination of aldehydes" Tetrahedron Letters, vol. 34, No. 10 (1993) pp. 1585-1588.

* cited by examiner

*Primary Examiner* — Fereydoun G Sajjadi
*Assistant Examiner* — Amy C Bonaparte
(74) *Attorney, Agent, or Firm* — Cesari and McKenna, LLP

(57) ABSTRACT

This invention relates to conjugated diene phosphinate compounds for making halogen free phosphinate-containing flame retardants, inimer and metal extractants, method for preparing said compounds from unsaturated ketones or aldehydes, and the 5 use thereof. The compounds of the present invention having the following formula (III), wherein $R_1$, $R_2$, $R_3$, $R_4$, $R_5$ and $R_6$ represent, independently, hydrogen, alkyl, aryl, alkaryl, aralkyl, cycloalkyl, heterocycloalkyl, or alkenyl groups; $R_7$ represents hydrogen, alkyl, aryl, alkaryl, aralkyl, cycloalkyl, alkenyl groups, or metals selected from the group consisting of Na, Li, Ca.

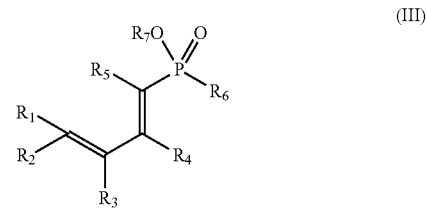

(III)

22 Claims, No Drawings

CONJUGATED DIENE PHOSPHINATE COMPOUNDS, PREPARATION METHOD AND USE THEREOF

CROSS REFERENCE TO RELATED APPLICATIONS

This application claims priority to international application no. PCT/CN2009/074730, filed Oct. 30, 2009. The contents of the aforementioned application are incorporated herein in their entirety.

TECHNICAL FIELD

This invention relates to new phosphinate diene compounds for making halogen free phosphinate-containing flame retardants, inimer and metal extractants, method for preparing the same from unsaturated ketones or aldehydes, and the use thereof.

BACKGROUND

Phosphinate species are typically difficult to prepare especially when the substituent group is unsaturated. The unsaturated species reported are typically alkenes with some rare examples of allenes. In any case, such species are difficult to prepare and typically require either multi-steps preparation or catalysis. In addition, the species generated such as the alkene phosphinates only have a limited reactivity in polymerization. As far as we know, no 1,3-diene phosphinate has been reported in the literature whereas such structure could have some very interesting reactivity.

The closest structures reported are 1,2-diene (aka allenes) such as in Russian papers (Antibiot. Ferm. Med. Naznachen., Leningrad, USSR. Doklady Akademii Nauk SSSR (1983), 269(6), 1377-80 OR Belakhov, V. V.; and al., Zhurnal Obshchei Khimii (1983), 53(7)). These allenes structures are synthesized from acetylenic alcohols and hypophosphorous acids.

In the literature the reactivity of α,β-unsaturated carbonyl compounds has been widely studied and Mauser (Chem. Rev., 1963, 63 (3), pp 311-324) specifically studied the reactivity of mesityl oxide. Typically such compounds can either react at the carbonyl or at the double bond. Usually, the reaction at the carbonyl with strong nucleophilic compounds such as Grignard reagents afford the corresponding hydroxyl adducts or the allenes (1,2-dienes) if the dehydration takes place. When the reactions take place at the double bond with other nucleophilic compounds such as amines or alcohols the mechanism is a 1,4 addition leading to the formation of the corresponding ketone. In particular the reaction of mesityl oxide with dialkylphosphites lead selectively to the formation of the ketones.

There are different types of inimers. For example, U.S. Pat. No. 6,156,859 described a cationic inimer to create hyperbranched iso-olefins U.S. application 2006-849415P uses halogenated inimers to make hyperbrached polymers by self-condensing vinyl ATRP (Atomic Transfer Radical Polymerization). However, the radical inimers, which is not easy to prepare, are halogenated compounds and metal co-initiator is required. Halogens are considered toxic and the use of metal often contaminates the polymers.

There is an increasing need for more efficient inimers, i.e., monomeric initiators, capable of creating hyperbranched polymer structures via different mechanisms (radical, catalytic etc . . . ). A H-phoshinate diene would provide a unique structure capable of playing such a role.

Today, metallic phosphinates is the leading technology to replace halogenated flame retardants. However, the main process to prepare this family of compounds is difficult and overall expensive. There is a real need to develop a new cost efficient chemistry allowing preparation of phosphinate or polymeric phosphinate that could be used as flame retardants. The leading chemistry to prepare dialkylphosphinate salts for use in flame retardants is based on Clariant chemistry (U.S. Pat. No. 6,329,544) which consists in reacting olefins with hypophosphorous acid under very harsh conditions. In particular the reaction of ethylene and hypophosphorous acid is widely used to prepare well known flame retardants. Another chemistry widely used as flame retardant is the DOPO that is a cyclic H-phosphinate and its chemistry is based on $PCl_3$. This chemistry is not ideal when trying to prepare halogen free flame retardants.

Phosphinate compounds are well known to be widely used in the mining industry to separate metals. There are some attempts to fix them on polymeric structures to enable to have solid supported extractants. However, this strategy is somehow expensive due to the difficulty to graft durably phosphinate groups on polymeric structures. H-phosphinate diene structures if they were available could allow designing some new polymeric structure having a high density of phosphinic groups thus allowing a good metallic separation.

SUMMARY OF THE INVENTION

In general, the present invention provides conjugated diene phosphinates of the formula III that can be used as inimer which can then allow access to new hyperbranched polymeric materials such as polyolefins, polystyrene, polybutadiene, poly(meth)acrylics and their copolymers. It can also be used to create hypobranched polyelectrolytes by radical addition such as polyacrylamide, polycarboxylates and its co-polymers. The present invention also provides the method for preparing conjugated diene phosphinates of the formula III.

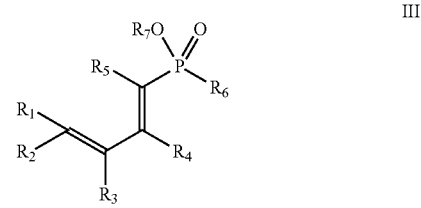

The polymers of conjugated diene phosphinates according to the present invention could find applications in water treatment, oilfield applications, surface treatment applications, mining, dental application, plastics, etc. The monomer could also be grafted onto synthetic or natural rubber.

Any polymeric structure prepared either from the isolated 1,3-diene phosphinate or its reaction mixture would bear some flame retardant and potentially anti-oxidant properties in the case of 1,3-diene H-phosphinates ($R_6$=H). Such material could be used in plastic industry to prepare halogen free flame retardant composition but also in textile or any other application requiring flame retardant properties.

Polymeric structures derived from the 1,3-diene H-phosphinate would also have some unique metal extraction properties that would allow developing a solid supported metal extraction process. The main application could be found in the mining industry to develop solvent less or solvent free metal extraction processes, in the nuclear industry that requires some highly efficient metal extractants to separate nuclear waste as well as in water treatment industry to remove heavy metals.

DETAILED DESCRIPTION OF THE INVENTION

In one aspect, the present invention provides conjugated diene phosphinate compounds having the formula III:

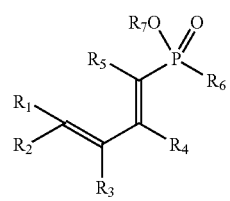

wherein, $R_1$, $R_2$, $R_3$, $R_4$, $R_5$ and $R_6$ represent, independently, hydrogen, alkyl, aryl, alkaryl, aralkyl, cycloalkyl, heterocycloalkyl, or alkenyl groups; preferably, the said alkyl, alkenyl comprise from 1~18 carbon atoms, said aryl comprises from 6~18 carbon atoms, said alkaryl, aralkyl comprise from 7~18 carbon atoms, and said cycloalkyl, heterocycloalkyl comprise from 3~18 carbon atoms.

Preferably, $R_1$ and/or $R_2$ represent hydrogen if a more reactive monomer is the target.

Preferably, $R_1$, $R_2$ and $R_4$ represent hydrogen; or $R_3$ and $R_5$ represent methyl; more preferably, $R_1$, $R_2$ and $R_4$ represent hydrogen, $R_3$ and $R_5$ represents methyl.

$R_7$ represents hydrogen, alkyl, aryl, alkaryl, aralkyl, cycloalkyl, alkenyl groups, or metals selected from the group consisting of Na, Li, Ca. preferably, the said alkyl, alkenyl comprise from 1~18 carbon atoms, said aryl comprises from 6~18 carbon atoms, said alkaryl, aralkyl comprise from 7~18 carbon atoms, and said cycloalkyl, heterocycloalkyl comprise from 3~18 carbon atoms.

In one of the preferred embodiments of the present invention, any two of $R_1$, $R_2$, $R_3$, $R_4$, $R_5$, $R_6$, and $R_7$ are together formed into a cycloalkyl, or heterocycloalkyl group, which is preferably selected from 3~8 membered rings.

Unless otherwise defined herein or below in the remainder of the specification, "Compounds of the present invention" or "compounds prepared according to the present invention" refers to compounds encompassed by the various description and structural formula disclosed herein. The compounds may be identified by either their chemical structure and/or chemical name.

The compounds of the present invention may contain one or more chiral centers and/or double bonds and therefore may exist as stereoisomers, such as Z- and E- or cis- and trans-isomers from cyclic structures or double bonds (i.e., geometric isomers), rotamers, enantiomers or diastereomers. Accordingly, when stereochemistry at chiral centers is not specified, the chemical structures depicted herein encompass all possible configurations at those chiral centers including the stereoisomerically pure form (e.g., geometrically pure, enantiomerically pure or diastereomerically pure) and enantiomeric and stereoisomeric mixtures, with the exception that when only one enantiomer is specified, the structure includes the other enantiomer as well. For example, in the event that a compound of formula III disclosed in the present invention is Z-form or trans-form for the double bond close to P, one skilled in this art should understand that the E-form or cis-form of the compound is also disclosed. Enantiomeric and stereoisomeric mixtures can be resolved into their component enantiomers or stereoisomers using separation techniques or chiral synthesis techniques well known to those skilled in this art.

In one other aspect, the present invention provides a method for preparing conjugated diene phosphinate compounds from α,β- or β,γ-unsaturated ketones or aldehydes, which comprises, reacting an α,β- or β,γ-unsaturated ketone or aldehyde having the formula I or II,

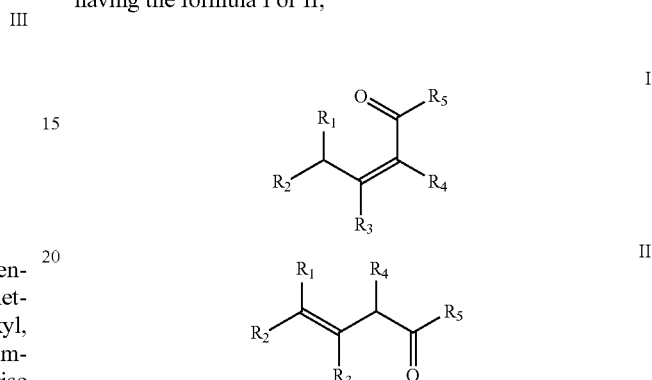

with a phosphinic acid or its derivatives having the formula,

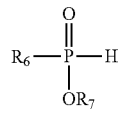

to obtain a conjugated diene phosphinate compound having the formula III,

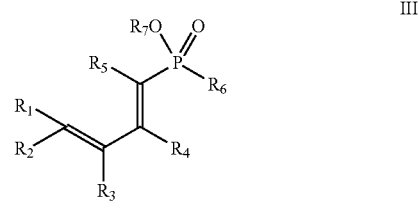

The process disclosed in the present invention allows to change the selectivity of the reaction of phosphinate compounds bearing at least one P—H bond to obtain selectively 1,3-diene compounds when starting from α,β or β,γ-unsaturated carbonyl compounds.

One potential mechanism to explain the selectivity of the reactions would be a concerted addition—dehydration mechanism with an oxaphosphirane intermediate (P—C—O membered ring). The presence of phosphinate and allylic protons could explain the ease of dehydration steps observed experimentally to afford the conjugated double bonds.

This one-step addition and dehydration mechanism could be depicted as below. Oxaphosphirane (P—C—O membered ring) is considered as an intermediate, followed by elimination and rearrangement to form the diene. Both the phosphinate and allylic proton facilitate the formation of the conjugated C=C double bonds:

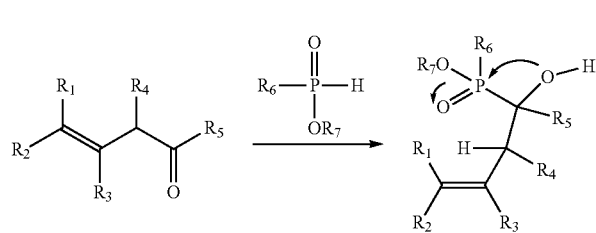

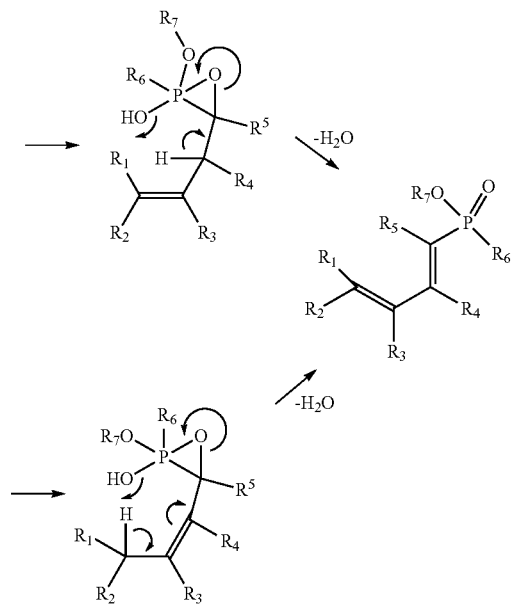

Without wishing to be bound by any existing theory, the preparation method of the present invention is valid whether starting from α,β-unsaturated carbonyl compounds or β,γ-unsaturated carbonyl compounds and both species will lead to the formation of the same diene.

According to the method of the present invention, said compound I or II is added in the molar ratio of (0.5~2):1 relative to said phosphorous acid or its derivatives; or preferably (1~1.5):1 relative to said phosphorous acid or its derivatives. Usually, the reaction is carried out in organic solvents such as solvent(s) selected from one or more of the group consisting of toluene, cyclohexane, butyl ether. The reaction time remains 4~24 hours, or preferably 4-8 hours. The reaction temperature remains 0~150° C., or preferably 85~125° C.

Preferably, the reaction is carried out under inert gas protection. Said inert gas may be selected from, for example, one or more of the group consisting of nitrogen, argon, and carbon dioxide.

For example, mesityl oxide, is reacted with hypophosphorous acid in its concentrated form to afford 4-methylpenta-2,4-diene-2-phosphinic acid. The same reaction could be carried out using 50% hypophosphorous acid using toluene as azeotropic solvent to remove water during the reaction. The target monomer can be easily isolated and purified by simple extractions and washes to obtain up to 97% pure product.

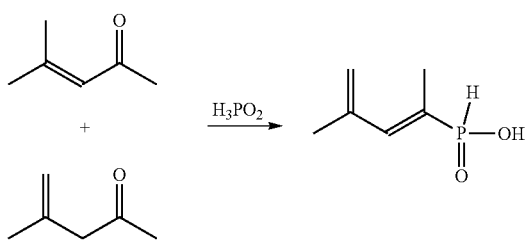

The process described above allows to form a mixture of phosphinate and phosphonate compounds that can be directly polymerized to obtain polymers containing both phosphinate and phosphonate groups in which both functionalities are well known to provide some useful properties such as flame retardant property.

The unsaturated ketones and aldehydes suitable for the present invention can be obtained from aldol condensations of ketones and aldehyde.

For example, dimerization of methyl isobutyl ketone (MIBK) as taught by U.S. Pat. No. 4,170,609.

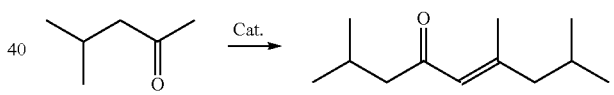

In a similar manner, aldol condensation of pinacolone will yield a highly branched unsaturated ketone:

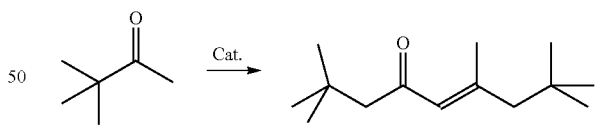

Some commercially available unsaturated ketones and aldehydes may also be used in the present invention. They are important industrial chemicals used as solvents, for example, mesityl oxide, precursor to other commodity and specialty chemicals, for example, isophorone and monomer for polymeric materials, for example, methyl vinyl ketone (MVK).

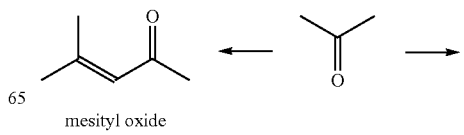

mesityl oxide

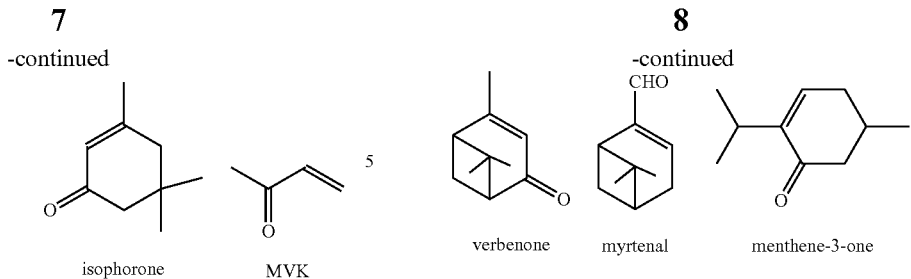

3-Methylcrotonaldehyde is a precursor for Vitamin A. Industrially, it is produced from isobutene and formaldehyde:

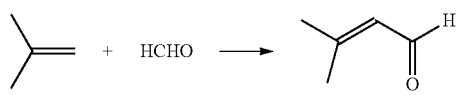

An attractive one may be crotonaldehyde. It is a biogenic compound, used for florvoring. It can be produced from renewable resources, bioethanol:

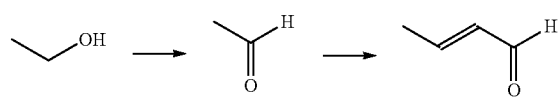

2-Ethyl acrolein, and its isomer of tiglic aldehydes are intermediate for flavor agents (U.S. Pat. No. 4,605,779):

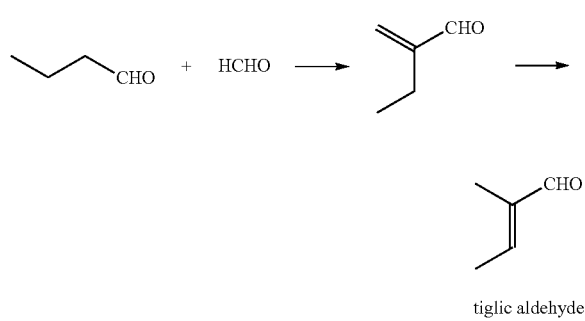

Natural unsaturated ketones and aldehydes could also be used in the preparation, for example, piperitone, carvone, umbellulone, menthene-2-one, menthene-3-one, verbenone and myrtenal. The resulting phosphinate diene could be of important biological activities, thus as insecticides, pesticides, pharmaceuticals and their intermediates.

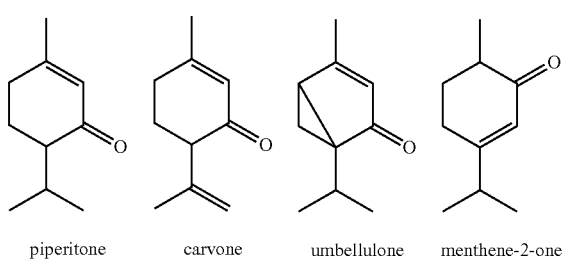

In one other aspect of the invention, the phosphinate diene according to the present invention can be used for making polymers or co-polymers. In this aspect the invention also relates to a polymer or co-polymer of said conjugated diene phosphinate compounds. The invention also relates to a method for preparing polymers or co-polymers of the phosphinate diene, comprising a step of preparing a phosphinate diene according to the method of the present invention and a polymerization or co-polymerization step.

In one other aspect, the present invention provides the use of phosphinate diene compounds according to the present invention.

The phosphinate diene prepared from aldehydes and ketones according to the present invention, or the polymer or co-polymer can be used as flame retardants, as intermediates for active pharmaceuticals and agrochemicals, as reactive or functional monomers, typically for functional polymers, such as phosphinate-containing polystyrene, polyethylene, polypropylene, poly(meth)acrylates, poly(meth)acrylamide, polybutadiene, polyacrylonitrile, etc. and their copolymers, or building blocks for other useful products. For example, but not to limit this invention, the phosphinate diene prepared according to the method of the present invention, or the polymer or co-polymer can be used in water treatment applications, in oilfield applications, in surface treatment applications, in mining applications, in dental applications, in plastics, and etc . . . . Preferably, the phosphinate diene according to the present invention, or the polymer or co-polymer can be used as flame retardants in plastics or textile. The invention also relates to methods comprising these uses.

The phosphinic monomer of the present invention itself is an inimer The P—H bonds serve as a radical inititor site for branching, which is illustrated as follows:

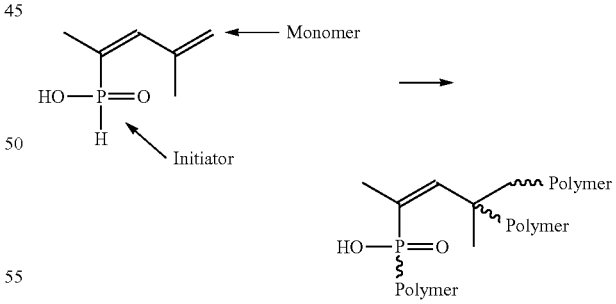

The phosphinic acid monomer can be homo-polymerized or co-polymerized with other monomer(s) into dialkyl phosphinate polymeric flame retardants or metal extractants. It is expected to polymerize under radical, anionic or cationic initiation. Therefore, the present invention also provides polymers or co-polymers of the compounds of formula III.

Advantages of the present invention are as follows:

1) The present invention provides a new class of organophosphinate, 1,3-diene-phosphinate and their derivatives in one step from α,β, or/and β,γ-unsaturated ketones or aldehydes. The reaction is carried out under very mild conditions and results in good yield and good purity.

2) The new compound according to the present invention opens a new type of chemistry to be available for new polymeric materials of hyper-branched structures, for pharmaceuticals and agrochemicals and their intermediates, for flame retardants, for extractants or heavy metal absorbents.

3) The technical solution of the present invention can be kind to the environment. Using sustainable and natural raw materials is critical today and many unsaturated ketones or aldehydes are actually natural products and can be derivatized from renewable resources such as ethanol.

The invention is further described by the examples below.

EXAMPLES OF THE PRESENT INVENTION

The following examples are offered to illustrate, but not to limit the present invention.

Example 1

In a 100 ml flask were added 16.5 g of hypophosphorous acid ($H_3PO_2$, 50% in water), 12.25 g of mesityl oxide (a mixture of 1,2- and 1,3- unsaturated ketone) and 20 ml toluene. Te mixture was heated under nitrogen to reflux at 125° C. overnight (around 17 hrs), the water was collected and separated out. $^{31}P$ NMR showed 86.4% $H_3PO_2$ was reacted and 4-methyl-2,4-pentadiene-2-phosphinic acid (PiDM) was obtained at 65.4% selectivity along with other minor impurities.

Example 2

Into a 500 ml flask was added 66 g $H_3PO_2$ (50% in water) , 49 g of mesityl oxide and 100 ml of toluene were added. The mixture was heated under nitrogen to reflux for 24 hours. $^{31}P$ NMR showed that 82.6% $H_3PO_2$ was reacted and 4-methyl-2,4-pentadiene-2-phosphinic acid (PiDM) was obtained at 68.5% selectivity along with other minor impurities after 6 hours of azeotropic distillation of water. The reaction was continued for 24 hours to get 97.3% conversion of $H_3PO_2$ and 44.4% selectivity to 4-methyl-2,4-pentadiene-2-phosphinic acid (PiDM). The reaction mixture was cooled down to room temperature and the leftover solvent was removed on a rotary evaporator. The residual was dissolved in 200 ml dichloromethane and the solution was washed with 100 ml of water three times. The combined dichloromethane phase was dried with anhydrous $Na_2SO_4$ and the solvent was evaporated to yield 46.5 g yellow viscous oil at a crude yield of 63.7% and purity of 71% PiDM.

Example 3

Process was similar to Example #2, except 16.5 g $H_3PO_2$ (50%), 24.5 g mesityl oxide and 20 ml of toluene were used instead. The reaction was carried out for 6 hours to reach 100% conversion for $H_3PO_2$ and 65.7% selectivity to PiDM.

Example 4

Into a 1 L three-necked round flask, protected under nitrogen, was charged with 107.8 g of mesityl oxide, 132 g of $H_3PO_2$ (50%) and 400 ml of toluene. The system was flushed with nitrogen and heated to reflux. Water was distilled out as azeotropic mixture with toluene. The reaction was continued for 20 hours until $^{31}P$ NMR showed all $H_3PO_2$ was consumed. The reaction mixture was cooled down to room temperature and washed with 400 ml of water and then the extracted with diluted NaOH solution. The aqueous phase was then acidified with 4 N HCl to pH 1 and back extracted with 50 ml dichloromethane. The organic phase was collected, dried over anyhydrous $Na_2SO_4$ and evaporated to give 68.5 g of bright yellow oil was. $^{31}P$ NMR showed 89.7% by mole was PiDM at a crude yield of 46.9%. The remaining P-containing compounds could be used as flame retardants.

Example 5

Into a 1 L three-necked round flask, protected with nitrogen, were charged with 98 g of mesityl oxide, 198 g of $H_3PO_2$ (50% in water) and 100 ml of toluene. The system was flushed with nitrogen and heated under reflux. Water was distilled out as azeotropic mixture with toluene. The reaction was refluxed overnight and then was cooled down. The solvent was removed on a rotary evaporator and then distilled under vacuum to yield 167 g green yellow viscous oil. $^{31}P$ NMR in $CDCl_3$ showed 73.3% conversion of $H_3PO_2$ and 44.9% selectivity to PiDM.

Example 6

Into a 500 ml flask were charged 111 g mesityl oxide, 100 g of $H_3PO_2$ (50% in water) and 150 ml of cyclohexane. The mixture was heated under nitrogen to reflux at 85° C. overnight while water was removed as azeotropic mixture. $^{31}P$ NMR showed 75.4% showed conversion of $H_3PO_2$ and 48% selectivity to PiDM.

Example 7

The procedure was the same as Example #6, except 100 ml of butyl ether was used instead of 150 ml cyclohexane. The mixture was heated under reflux at 130° C. overnight while water was removed. The mixture turned to be a clear yellow solution. After it was cooled down to room temperature, phases separation was observed, the upper layer was light yellow, butyl ether solvent, the lower layer was yellow viscous product mixture. $^{31}P$ NMR 96.1% showed conversion of $H_3PO_2$ and 52.9% selectivity to PiDM.

Example 8

24.5 g of mesityl oxide, 0.12 g of 98% $H_2SO_4$ and 50 ml toluene were added into a 100 ml three necked flask under nitrogen. The mixture was heated to reflux at 125° C. with zeotropic distillation of water. 16.5 g of $H_3PO_2$ (50% aqueous solution) was added drop-wise over 2 hours. After the addition, the reaction was continued for another 6 hours. The obtained reaction mixture showed 98.4% conversion of hypophosphorous acid and 73.9% selectivity to PiDM. PiDM increased to 78.3% after the mixture was washed with 50 ml of water three times. Further purification was done by extract the organic phase with water at pH 5 adjusted by NaOH or HCl solution to increase the purity to 96.1% by mole. The aqueous phase was acidified again to pH 1 with HCl and back extracted with dichlormethane to yield DiPM of 97.7% (by mole with $^{31}P$ NMR) after evaporation of the solvent. $^{31}P$ NMR (d6-DMSO, ppm): 25.4 (PiDM 97.7%), 39.6 (unknown, 2.3%). $^1H$ NMR (d6-DMSO, δ ppm): 7.51 & 6.43 (2s, 1H), 6.60 (d, 1H), 5.24 (s, 1H), 5.09 (s, 2H), 1.93 (s, 3H), 1.91 (d, 3H). $^{13}C$ (d6-DMSO, δ ppm), δ 140.4 & 140.2 (d), 140.1 & 140.0 (d), 130.8 & 129.8 (d), 119.9, 22.3, 12.2 & 12.1 (d).

Example 9

33 g of $H_3PO_2$ (50%) was concentrated on a rotary evaporator up to about 80-90% w/w. Then 49 g of mesityl oxide 0.8 g phenothiazine were added into the flask, the mixture was degassed with $N_2$ and heated to reflux (110° C.). After 4 hours, 100% of $H_3PO_2$ was consumed to form 55% of PiDM.

Example 10

16.5 g $H_3PO_2$ (50%) was concentrated on a rotary evaporator up to about 80-90% w/w. Then 12.25 g of mesityl oxide and 0.2 g phenothiazine were added into the flask, the mixture was degassed with $N_2$ and heated to reflux. After 7 hours the conversion of $H_3PO_2$ was complete. The mixture was cooled down to room temperature and 50 ml of dichloromethane was added into the mixture. The solution was washed with 50 ml of water three times. The organic phase was dried by anhydrous $Na_2SO_4$ and the solvent was removed under reduced pressure to afford 8.1 g of clear yellowish viscous oil. Total yield: 44.4%

Example 11

4-Methyl-2,4-pentadiene-2-phosphinic acid (DiPM) 10 g from Example 4, and 50 ml of isopropanol propanol were charged into a 100 ml three-necked flask. The mixture was stirred at room temperature to obtain a clear light yellow solution. Then 7.7 g of melamine was charged into the reactor and the mixture became milky and was difficult to stir. The mixture was heated to 85° C. and 0.1 g of AIBN (azobisisobutyronitrile), was added in one portion. Polymer was obtained as white precipitated solid. The dried solid did not sustain flame burning after taken off a flame burner.

Example 12

4-Methyl-2,4-pentadiene-2-phosphinic acid (DiPM) 10 g from Example 4, and 10 ml of water were charged into a 100 ml three-necked flask. The mixture was stirred at room temperature to obtain a clear light yellow solution. Then 2.3 g of $Al(OH)_3$ was charged into the reactor and the mixture was heated at 50° C. with stirring for 30 minutes to yield a suspension. Initiator of 0.2 g $Na_2S_2O_8$ was added and then heated at 100° C. for 4 hours, and another portion of 0.2 g $Na_2S_2O_8$ was added into the mixture and aged overnight to yield the polymer. The dried solid did not sustain flame burning after taken off a flame burner.

EXAMPLE 13

Polymer was also obtained by auto polymerization of purified PiDM from Example 4 at room temperature. Polymer was isolated by precipitation from toluene. Thus PiDM 40 g was dissolved into 100 ml of toluene. 0.1 g of AIBN (azobisisobutyronitrile) was charged in 3 portions under nitrogen atmosphere at 80° C. over 3 hours. Stirred for further 1 hour at the same temperature, then the precipitates was filtered and dry to obtain 30 g pale yellow solid polymer. The polymer was cured in 10% NaOH solution for 2 days and then turned into a water-swelled gel. The gel was demonstrated to absorb copper (II) ion in $CuSO_4$ solution to become blue, leaving the aqueous phase colorless.

What is claimed is:

1. A conjugated diene phosphinate compound having the formula III:

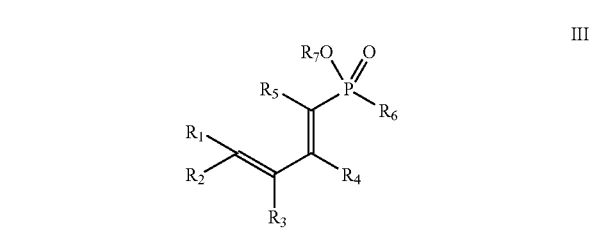

wherein,
$R_1$, $R_2$, and $R_4$ each represent, independently, hydrogen, alkyl, aryl, alkaryl, aralkyl, cycloalkyl, heterocycloalkyl, or alkenyl;
$R_3$ and $R_5$ each represent methyl;
$R_6$ and $R_7$ each represent hydrogen;
and optionally wherein any two of $R_1$, $R_2$, $R_3$, $R_4$, and $R_5$ form a 3-8 membered cycloalkyl or heterocycloalkyl ring.

2. The conjugated diene phosphinate compound according to claim 1, wherein the said alkyl and alkenyl each comprise 1~24 carbon atoms, said aryl comprises 6~24 carbon atoms, said alkaryl and aralkyl each comprise 7~24 carbon atoms, and said cycloalkyl or heterocycloalkyl ring comprises 3~24 carbon atoms.

3. The conjugated diene phosphinate compound according to claim 1, wherein the said alkyl and alkenyl each comprise 1~18 carbon atoms, said aryl comprises 6~18 carbon atoms, said alkaryl and aralkyl each comprise 7~18 carbon atoms, and said cycloalkyl or heterocycloalkyl ring comprises 3~18 carbon atoms.

4. The conjugated diene phosphinate compound according to claim 1, wherein at least one of $R_1$ and $R_2$ is hydrogen.

5. The conjugated diene phosphinate compound according to claim 1, wherein any two of $R_1$, $R_2$, $R_3$, $R_4$, and $R_5$ form a 3-8 membered cycloalkyl or heterocycloalkyl ring.

6. The conjugated diene phosphinate compound according to claim 1, wherein $R_1$, $R_2$ and $R_4$ each represent hydrogen.

7. A method for preparing a conjugated diene phosphinate compound from an α,β- or β,γ-unsaturated ketone or aldehyde, which comprises reacting an α,β- or β,γ-unsaturated ketone or aldehyde having the formula I or II,

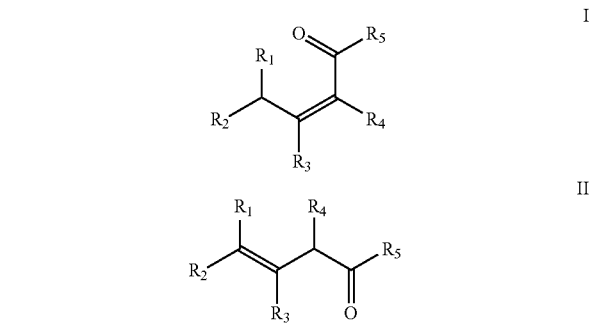

with a phosphinic acid having the formula,

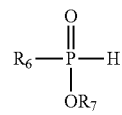

to obtain a conjugated diene phosphinate compound having the formula III,

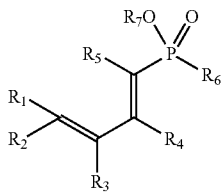

III wherein,

R$_1$, R$_2$, and R$_4$ each represent, independently, hydrogen, alkyl, aryl, alkaryl, aralkyl, cycloalkyl, heterocycloalkyl, or alkenyl;

R$_3$ and R$_5$ each represent methyl;

R$_6$ and R$_7$ each represent hydrogen;

and optionally wherein any two of R$_1$, R$_2$, R$_3$, R$_4$, and R$_5$ form a 3-8 membered cycloalkyl or heterocycloalkyl ring.

8. The method according to claim 7, wherein the said alkyl and alkenyl each comprise 1~24 carbon atoms, said aryl comprises 6~24 carbon atoms, said alkaryl and aralkyl each comprise 7~24 carbon atoms, and said cycloalkyl or heterocycloalkyl ring comprises 3~24 carbon atoms.

9. The method according to claim 7, wherein the said alkyl and alkenyl each comprise 1~18 carbon atoms, said aryl comprises 6~18 carbon atoms, said alkaryl and aralkyl each comprise 7~18 carbon atoms, and said cycloalkyl or heterocycloalkyl ring comprises 3~18 carbon atoms.

10. The method according to claim 7, wherein at least one of R$_1$ and R$_2$ is hydrogen.

11. The method according to claim 7, wherein any two of R$_1$, R$_2$, R$_3$, R$_4$, and R$_5$ form a 3-8 membered cycloalkyl or heterocycloalkyl ring.

12. The method according to claim 7, wherein R$_1$, R$_2$, and R$_4$ each represent hydrogen.

13. The method according to claim 7, wherein said compound I or II is added in the molar ratio of (0.5~2):1 relative to said phosphinic acid.

14. The method according to claim 13, wherein said compound I or II is added in the molar ratio of (1~1.5):1 relative to said phosphinic acid.

15. The method according to claim 7, wherein the reaction is carried out in a solvent selected from the group consisting of toluene, cyclohexane, butyl ether, and a combination thereof.

16. The method according to claim 7, wherein the reaction is carried out under inert gas protection.

17. The method according to claim 16, wherein said inert gas is selected from the group consisting of nitrogen, argon, carbon dioxide, and a combination thereof.

18. The method according to claim 7, wherein the reaction temperature is 0° C.~150° C.

19. The method according to claim 18, wherein the reaction temperature is 85° C.~125° C.

20. The method according to claim 7, wherein the reaction time is 4~24 hours.

21. The method according to claim 20, wherein the reaction time is 4~8 hours.

22. A polymer or co-polymer of the compound of formula III according to claim 1.

* * * * *